(12) United States Patent
Taylor et al.

(10) Patent No.: US 6,784,171 B2
(45) Date of Patent: Aug. 31, 2004

(54) PROCESS FOR THE PRODUCTION OF TERT-BUTYL (E)-(6-[2-[4-(4-FLUOROPHENYL)-6-ISOPROPYL-2-[METHYL(METHYLSULFONYL)AMINO] PYRIMIDIN-5-YL]VINYL](4R,6S)-2, 2-DIMETHYL[1, 3]DIOXAN-4-YL)ACETATE

(75) Inventors: Nigel P Taylor, Macclesfield (GB); Loius J Diorazio, Macclesfield (GB); Haruo Koike, Amagasaki (JP); Mikio Kabaki, Amagasaki (JP)

(73) Assignee: AstraZeneca, Sodertalje (SE)

( * ) Notice: Subject to any disclaimer, the term of this patent is extended or adjusted under 35 U.S.C. 154(b) by 0 days.

(21) Appl. No.: 10/610,700

(22) Filed: Jul. 2, 2003

(65) Prior Publication Data

US 2004/0049036 A1 Mar. 11, 2004

Related U.S. Application Data

(63) Continuation of application No. 09/913,539, filed as application No. PCT/GB00/00481 on Feb. 15, 2000.

(30) Foreign Application Priority Data

Feb. 17, 1999 (GB) .............................................. 9903472

(51) Int. Cl.$^7$ ...................... A61K 31/33; C07D 239/34; C07D 239/38; C07D 239/42
(52) U.S. Cl. ...................... 514/183; 514/256; 544/322; 544/316; 544/318
(58) Field of Search ................................. 514/183, 256; 544/322, 316, 318

(56) References Cited

U.S. PATENT DOCUMENTS 5,260,440 A * 11/1993 Hirai et al. .................. 544/332

FOREIGN PATENT DOCUMENTS

| EP | 0319847 | 6/1989 |
|---|---|---|
| EP | 0521471 | 1/1993 |
| WO | 97/19917 | 6/1997 |

OTHER PUBLICATIONS

Wess et al., "Stereoselective Synthesis of HR 780 A New Highly Potent HMG–CoA Reductase Inhibitor", Tetrahedron Letters, vol. 31, No. 18, 1990, pp. 2545–2548.
Minami et al., "A Novel Enantioselective Synthesis of HMG Co–A Reductase Inhibitor NK–104 and a Related Compound", Tetrahedron letters, vol. 33, No. 49, 1992, pp. 7525–7526.
Minami et al., "Stereoselective Reduction of β,δ–Diketo Esters Derived From Tartaric Acid. A Facile Route to Optically Active 6–oxo–3,5–syn–isopropylidenedioxyhexanoate, a Versatile Synthetic Intermediate of Artificial HMG Co–A Reductase Inhibitors", Tetrahedron Letters, vol. 34, No. 3, 1993, pp. 513–516.
Hiyama et al., "Synthesis of Artificial HMG–CoA Reductase Inhibitors Based on the Olefination Strategy", Bull. Chem. Soc. Jpn., vol. 68, No. 1 1995, pp. 364–372.
Watanabe et al., "Synthesis and Biological Activity of Methanesulfonamide Pyrimidine– and N–Methanesulfonly Pyrrole–Substituted 3,5–Dihydroxy–6–heptenoates, a Novel Series of HMG–CoA Reductase Inhibitors", Bioord. Med. Chem., vol. 5, No. 2, 1997, pp. 437–444.
Prasad et al., "A Novel Diasteroselective Sythesis of Lactone Moie of Compactin";Tetrahedron Letters, vol. 25, No. 23, 1984, pp.24352438.
Solladié et al., "Chrial Sulfoxidesin Asymmetric Synthesis: Enantioselective Synthesis of the Lactonic Molety of (+)–Compactin and (+) Mevinolin. Application of a Compactin Analogue", J. Org. Cem. 1995, 60, pp. 7774–7777.

* cited by examiner

Primary Examiner—Mukund L. Shah
Assistant Examiner—Sudhaker B. Patel
(74) Attorney, Agent, or Firm—Morgan, Lewis & Bockius LLP

(57) ABSTRACT

The invention concerns a process for the manufacture of tert-butyl (E)-(6-[2-4-(4-fluorophenyl)-6-isopropyl-2-[methyl(methylsulfonyl)amino]pyrimidin-5-yl]vinyl)-(4R, 6S)-2,2-dimethyl(1,3-dioxan-4-yl) acetate, the novel starting material used in said process and the use of the process in the manufacture of a pharmaceutical.

11 Claims, No Drawings

PROCESS FOR THE PRODUCTION OF TERT-BUTYL (E)-(6-[2-[4-(4-FLUOROPHENYL)-6-ISOPROPYL-2-[METHYL(METHYLSULFONYL)AMINO] PYRIMIDIN-5-YL]VINYL](4R,6S)-2, 2-DIMETHYL[1, 3]DIOXAN-4-YL)ACETATE

This is a Continuation of copending Application No. 09/913,539, filed Dec. 7. 2001; which is a PCT National Phase Application of PCT/00/00481 filed Feb. 15, 2000, which claims priority to GB application No. 9903472.0 filed Feb. 17, 1999. Each listed U.S. Patents and/or application is entirely incorporated herein by reference in its entirety.

This invention concerns a novel chemical process, and more particularly it concerns a novel chemical process for the manufacture of tert-butyl (E)-(6-{2-[4-(4-fluorophenyl)-6-isopropyl-2-[methyl(methylsulfonyl)amino]pyrimidin-5-yl]vinyl}(4R,6S)-2,2dimethyl[1,3]dioxan-4-yl)acetate of formula I, Formula I

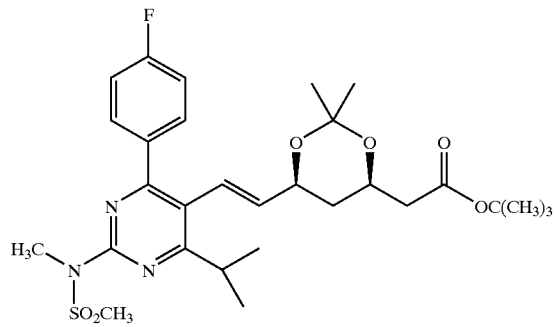

(hereinafter referred to as BEM) which is useful, for example, as a chemical intermediate in the production of a pharmaceutical useful in the treatment of, inter alia, hypercholesterolemia, hyperlipoproteinemia and atherosclerosis. The invention further includes the novel starting material used in said process and the use of the process in the manufacture of an HMG CoA reductase inhibitor.

In European Patent Application, Publication No. (EPA) 0521471 is disclosed (E)-7-[4(4-fluorophenyl)-6-isopropyl-2-[methyl(methylsulfonyl)amino]pyrimidin-5-yl](3R,5S)-3, 5dihydroxyhept 6-enoic acid and its sodium salt and calcium salt (illustrated below)

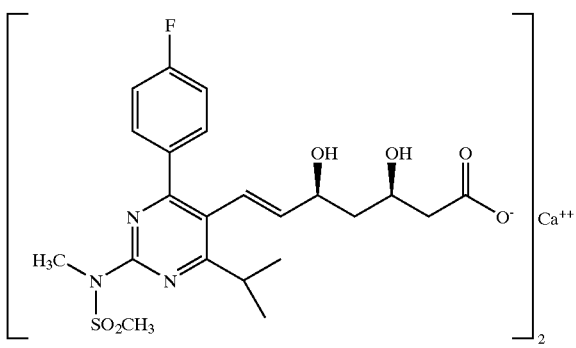

(hereinafter referred to collectively as "The Agent") as inibitors of HMG CoA reductase. The Agent is obtained therein via reduction of methyl 7-[4-(4-fluorophenyl)-6-isopropyl-2-(N-methyl-N-methylsulfonyl-amino)pyrimidin-5-yl-(3R)-3-hydroxy-5-oxo-(E)-heptenoate and subsequent processing. However the Agent may be obtained from BEM by treatment with acid (to cleave the acetonide protecting group) followed by base (to cleave the ester) and (as described in EPA 0521471) conversion of the initially formed salt to the free acid or the calcium salt.

We have now discovered a useful and advantageous process for preparing BEM.

According to the invention there is provided a process for preparing BEM (formula I) which comprises reaction of diphenyl [4-(4-fluoropheny)-6-isopropyl-2-[methyl (methylsulfonyl)amino]pyrimidin-5-ylmethyl] phosphine oxide of formula III Formula III

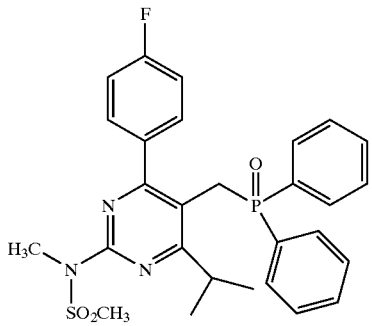

(hereinafter referred to as DPPO) with tert-butyl 2-[(4R,6S)-6-formyl-2,2-dimethyl-1,3-dioxan-4-yl}acetate of formula II Formula II

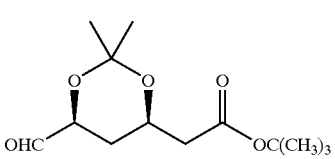

(hereinafter referred to as BFA) in the presence of a strong base.

The process is carried out in a suitable solvent, or mixture of solvents for example, ethereal or aromatic solvents or mixtures thereof. Particularly suitable solvents include, for example, tetrahydrofuran (THF), dimethoxyethane and toluene, or mixtures thereof. Particularly preferred solvents include, for example, THF and THF and toluene.

Suitable bases for use in the process include, for example, amide bases, alkyl metals and metal hydrides. Particular bases include, for example, sodium bis(trimethylsilyl) amide, potassium bis(trimethylsilyl)amide, lithium bis (trimethysilyl)amide, butyllithium and sodium hydride. A particularly preferred base is, for example, sodium bis (trimethylsilyl)amide (NaHMDS).

The reaction may be carried out at a temperature in the range of, for example, −20° C. to −90° C., such as −40° C. to −90° C., for example −40° C. to −80° C. A convenient tempreture at which to carry out the reaction is, for example, that of a mixture of acetone and solid carbon dioxide (about −75° C.).

The process is advantageously carried out with 1.0 to 1.2 equivalents of base (per equivalent of DPPO), such as 1.05 to 1.2 equivalents and preferably 1.05 to 1.12 equivalents. Although BFA can be present in large excess, it is convenient to use 1.0 to 1.35 equivalents (per equivalent of DPPO), and preferably 1.05 to 1.3 equivalents, especially 1.05 to 1.15 equivalents.

The process of the invention provides significantly improved yields and quality of product by comparison to when a corresponding dialkyl phosphonate (—PO(Oalkyl)$_2$) starting material is used instead of DPPO.

The starting material, DPPO, which is a further aspect of the present invention, may be obtained as described in the Examples hereinafter, starting from an alkyl 2-amino-4-(4-fluorophenyl)-6-isopropylpyrimidin-5-carboxylate, for example the methyl ester which may be obtained as described in Japanese Patent Application No. 06-256318, or the ethyl ester which may be obtained as described in EPA 0521471. BFA may be obtained as described in EPA 0319847 (Example 6).

A further aspect of the present invention is a process for the manufacture of a compound of the formula IV Formula IV

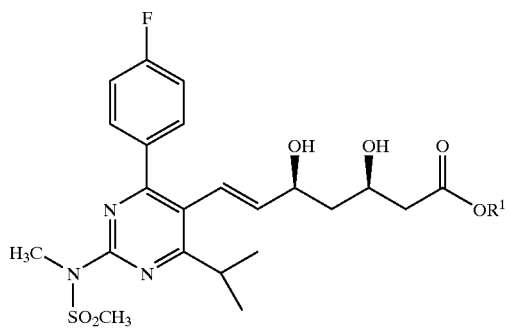

in which R$^1$ is hydrogen or a pharmaceutically acceptable cation, which comprises;
(1) reaction of DPPO with BFA in the presence of a strong base (as described above) to give BEM;
(2) cleavage of the dihydroxy (acetonide) protecting group (for example by acid hydrolysis, such as by using HCl in THF or acetonitrile); and
(3) cleavage of the tert-butyl ester group under basic conditions to form a compound of the formula IV in which R$^1$ is a pharmaceutically acceptable cation (for example by using a solution of a metallic hydroxide in a polar solvent, such as using aqueous sodium hydroxide in ethanol or acetonitrile to form the sodium salt);
optionally followed by neutralisation to give a compound of the formula IV in which R$^1$ is hydrogen;
and/or optionally followed by conversion to another compound of the formula IV in which R$^1$ is a pharmaceutically acceptable cation (for example conversion of the sodium salt to the calcium salt by treatment with a water soluble calcium salt (such as calcium chloride) under aqueous conditions).

Suitable conditions for steps (2), (3) and the subsequent optional steps are analogous to, or the same as, those disclosed in EPA 0521471 and/or EPA 0319847, which are hereby incorporated herein by reference. To obtain the calcium salt of the compound of formula IV, as illustrated on page 1, preferably steps (2), (3) and conversion to the calcium salt via the methylamine salt are carried out as described in Example 7, which steps form a further aspect of the invention.

It will be appreciated that, in the processes described above, BFA may replaced by a compound of the general formula V Formula V

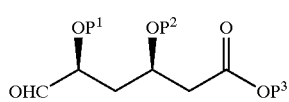

in which P$^3$ is a carboxylic acid protecting group, for example (1–8C)alkyl (such as 1–4C)alkyl), and P$^1$ and P$^2$ are alcohol protecting groups, or P$^1$ and P$^2$ taken together is a 1, 3-diol protecting group, such as those described in EPA 0319845 and GB 2244705 which are included herein by reference. For example, in some preferred embodiments, the 1,3-dial protecting groups can be

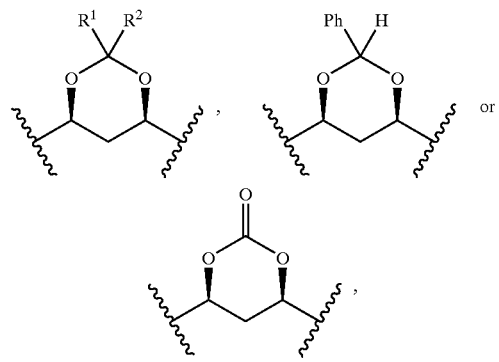

where R$^1$ and R$^2$ are independently (1–4C)alkyl or R$^1$ and R$^2$, taken together with the carbon atom to which they are attached, form a cyclopentyl. cyclohexyl or cycloheptyl ring. Reaction of a compound of the formula V with a compound of the formula III forms a compound of the formula VI Formula VI

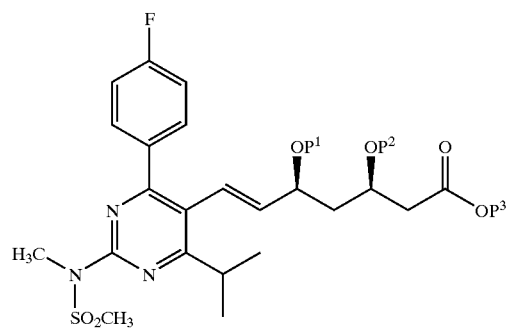

The compound of the formula VI may be converted to the Agent by cleavage of the alcohol or diol protecting groups and conversion of the COOP$^3$ to a COOH group or a pharmaceutically acceptable salt thereof. Such general processes form further features of the present invention.

The invention if further illustrated, but not limited by the following Examples.
Preparation 1
Preparation of DPPO A stirred mixture of methyl 4-(4-fluorophenyl)-6-isopropyl-2-[methyl(methylsulfonyl)amino]pyrimidine-5-carboxylate (12.0 g) in toluene (55 ml) was cooled to −10° C. and diisobutyl aluminium hydride (50 ml of a 1.5M solution in toluene) was added over two hours maintaining the temperature below 0° C. After addition, the mixture was stirred for 30 minutes at 0° C. Methanol (0.64 ml) was added to the mixture maintaining the temperature at 0° C. The mixture was then added over two hours to a stirred mixture of concentrated hydrochloric acid (23.3 ml), water (40.5 ml) and acetonitrile (24 ml) at 40° C., maintaining the temperature of the mixture at 40° C. After addition, the mixture was stirred at 40° C. for a further 30 minutes and then purged with nitrogen (to remove any isobutane). The mixture was cooled to 20° C. and allowed to stand for 20 minutes. The organic phase was separated and washed with a mixture of concentrated hydrochloric acid (0.7 ml) and water (30 ml). Acetonitrile (24 ml) was added to the organic phase and the mixture washed with a solution of sodium bicarbonate (0.038 g) in water (120 ml).

The organic phase was heated to 40° C., and then from 40° C. to 80° C. using a nitrogen purge. The mixture was concentrated by distillation at atmospheric pressure, collecting 54 ml of distillate. Acetonitrile (24 ml) was added to the concentrated solution and phosphorus tribromide (1.2 ml) was added with stirring, maintaining the temperature of the mixture at 20° C. After addition, the mixture was stirred at 20° C. for 30 minutes. The mixture was added to water (36 ml) over 30 minutes maintaining the temperature at 20° C. The mixture was stirred for 5 minutes and the organic phase separated. The organic phase was washed with a solution of sodium bicarbonate (0.027 g) in water (36 ml), followed by water (36 ml). The organic phase was distilled under reduced pressure until 29 ml of distillates was collected. The mixture was cooled to 60° C. and ethyl diphenylphosphinite (7.47 ml) was added. The mixture was stirred at 60° C. for 3 hours, then heated to reflux. Toluene (40 ml) was added and the mixture cooled to 0° C. over 2 hours. The product was collected by filtration, washed with cold toluene (10 ml) and dried under vacuum at 50° C. to give DPPO (14.66 g); $^1$HNMR (CDCl$_3$, 270 MHz): 7.42 [m, 10H, P(C$_6$H$_5$)$_2$], 7.12 [m, 2H, Ar—H], 6.92 [m, [d,2H, CH$_2$P], 3.51, 3.46 (2× s, 6H, NCH, SO$_2$CH$_3$], 3.43 [hept., 1H, CH(CH$_3$)$_2$],1.25[d, 6H, CH(CH$_3$)$_2$],1.25[d,6H, CH(CH$_3$)$_2$]

Methyl 4-(4-fluorophenyl)-6-isopropyl-2-[methyl (methylsulfonyl)amino)pyrimidine-5-carboxylate was prepared as follows:

A mixture of methyl 2-amino-4-(4-fluorophenyl)-6-isopropyl-pyrimidine-5-carboxylate (19.0 g), sodium tert-pentoxide (22.95 g) and dimethoxyethane (190 ml) was stirred for 30 minutes at 25° C. The stirred mixture was cooled to −10° C. and methanesulfonyl chloride (8.4 ml) was added dropwise, maintaining the temperature of the mixture at −5° C. After 20 minutes, dimethyl sulfate (8.1 ml) was added and the mixture allowed to warm to 25° C. The mixture was stirred for one hour at 25° C. and a solution of sodium tert-pentoxide (1.91 g) in dimethoxyethane (10 ml) added. The mixture was stirred for one hour at 25° C. A solution of sodium chloride (13.3 g) in water (133 ml) was added and the mixture was stirred for 10 minutes at 25° C. The mixture was allowed to settle for 15 minutes and the lower aqueous phase was separated and discarded. Water (38 ml) was added to the remaining mixture and the mixture was stirred for 30 minutes at 25° C. The mixture was then heated to obtain a complete solution. The mixture was cooled slowly to 25° C. over one hour. The mixture was cooled to 0° C., stirred for one hour, and the suspended solid collected by filtration. The solid was washed with cold (0° C.) solution of 50:50 water/dimethoxyethane (20 ml). The solid was dried under vacuum at 60° C. to give methyl 4-(4-fluorophenyl)-6isopropyl-2-[methyl(methylsulfonyl)amino] pyrimidine-5-carboxylate (19.35 g); $^1$HNMR (270 MHz, CDCl$_3$): 7.69 (m,2H), 7.14 (m,2H), 3.71, 3.60, 3.51(3× s, 9H), 3.20 (m, 1.(d,6H).

EXAMPLE 1

A mixture of DPPO (19.17 g) and THF (227 ml) were warmed briefly to 40° C. until a clear solution had formed then inerted by the sequential application of vacuum and nitrogen (5 cycles). The mixture was immersed in an acetone/CO$_2$ bath cooling the contents to −75° C. Sodium bis(trimethylsilyl)amide (37.4 ml of 1.0M solution in THF) was added to the reaction mixture over 10 minutes from a pressure equalising dropping funnel maintaining the temperature below −74° C. and forming a red solution of the anion. THF (10 ml) was rinsed through the dropping funnel into the mixture and the mixture stirred a further 1 hour at −76° C. forming a red suspension. BFA (80 ml of ~13.5% w/w toluene solution) was added in portions to the suspension over 20 minutes from a pressure equalising dropping funnel maintaining the temperature below −73° C. Toluene (20 ml) was rinised through the dropping funnel into the mixture and the mixture stirred a further 15 minutes at −76° C. The chilling bath was lowered and the suspension allowed to warm to 10° C. over 1.5 hours. Glacial acetic acid (3.21 g) in water (15 g) was added in one portion raising the temperature to 18° C. and dissolving all solids and the mixture was stirred a further 5 minutes.

The mixture was concentrated by distillation at atmospheric pressure (jacket 110° C.) to a temperature of 94° C. collecting a total of 274 ml distillates. The concentrated mixture was cooled to 40° C., water (40 ml) was added and the mixture stirred for 5 minutes then allowed to settle for 15 minutes. The lower aqueous phase was discarded. Sodium hydrogen carbonate (2.99 g) in water (40 ml) was added and the mixture stirred for 5 minutes then allowed to settle for 15 minutes. The lower aqueous phase was discarded. Water (30 ml) was added and the mixture stirred for 5 minutes then allowed to settle for 15 minutes. The lower aqueous phase was discarded.

The organic phase was transferred to a distillation apparatus with toluene (20 ml) and concentrated by distillation at atmospheric pressure (jacket 125–130° C.) to a temperature of 116° C. collecting 85 ml distillates. Vacuum was applied (400–500 mbar) and a further 16.5 ml distillates collected to a temperature of 111° C. The vacuum was released and the concentrated mixture allowed to cool to 80° C. Warm MeOH (140 ml, 50° C.) was added with rapid stirring and the batch allowed to self-cool to 20° C. over 30 minutes during which time a solid was deposited. The suspension was further cooled to 2° C. for 30 minutes then the solid was collected by filtration on a sinter and pulled as dry as possible. The solid was washed with cold MeOH (60 ml, 2° C.) and again pulled as dry as possible then transferred to a vacuum oven and dried overnight (50° C., 200 mbar); giving BEM (14.01 g, 67.7%).

$^1$H NMR (CDCl$_3$, 270 MHz)7.65 [m, 2H, Ar—H], 7.09 [m, 2H, Ar—H], 6.52 [dd, 1H, ArCH=CH], 3.57, 3.50 [2× s, 6H, NCH$_3$, SO$_2$CH$_3$], 3.38 [hept., 1H, Ar—CHMe$_2$],2.45, 2.30[2x dd, 2H, CH$_2$CO$_2$tBu], 1.55, 1.13 [dt, dd, 2H, acetonide CH$_2$], 1.50, 1.40 [2 x s, 6H,acetonide C(CH$_3$)$_2$], 1.45 [s, 9H, CO$_2$C(CH$_3$)$_3$], 1.27 [dd 6H, ArCH(CH$_3$)$_2$]

EXAMPLES 2–6

The procedure as described in Example 1 was carried out using the ratios of reactants and the temperatures given in Table 1. There was thus obtained BEM in the yields given.

TABLE 1

| Wt DPPO | Temp. (° C.) | Eq. NaHMDS | Eq. BFA | BEM Yield |
|---|---|---|---|---|
| 10.00 g | −75 | 1.12 | 1.20 | 69.2% |
| 18.12 g | −75 | 1.12 | 1.20 | 69.6% |
| 12.08 g | −75 | 1.06 | 1.26 | 72.8% |
| 19.17 g | −40 | 1.05 | 1.06 | 56.7% |

TABLE 1-continued

| Wt DPPO | Temp. (° C.) | Eq. NaHMDS | Eq. BFA | BEM Yield |
|---|---|---|---|---|
| 9.57 g | −90 | 1.05 | 1.10 | 72.0% |
| 9.57 g | −60 | 1.05 | 1.10 | 70.1% |

EXAMPLE 7

A mixture of BEM (5.0 g) and acetonitrile (35 ml) was stirred under an inert atmosphere at 40° C. 0.02M hydrochloric acid (9.5 ml) was added over 30 minutes to the resultant solution, maintaining the temperature at 35° C. to 42° C. The mixture was stirred at 40° C. for 3 hours then cooled to 25° C. 1.0M sodium hydroxide solution (9.5 ml) was added with stirring at 25° C. and the mixture was stirred for an additional one hour at 25° C. Sodium chloride (4.7 g) was added and the mixture was cooled to −5° C. over one hour. Sufficient of a solution of 1M hydrochloric acid (9.5 ml) and sodium chloride (2.4 g) was added at −5° C. to achieve a pH of 3.4 to 4.0 and the mixture stirred at this temperature for 5 minutes. The mixture was allowed to settle for 10 minutes at −5° C. to give two layers. The lower layer was separated and discarded. Acetonitrile (65 ml) at −5° C. was added to the remaining solution and the mixture was filtered through a filter agent. 40% methylamine solution in water (1.1 ml) was added at −5° C. and the mixture was warmed to 30° C. over 40 minutes and maintained at this temperature for 90 minutes. The mixture was then cooled to 0° C. over 40 minutes and maintained at this temperature for 90 minutes. The resultant solid was collected by filtration and washed with acetonitrile (2×12 ml). The solid, which is the methylamine salt of the compound of formula IV ($R^1$=MeNH$_3^+$), was dried under vacuum at 35° C. (3.87 g). 8% w/w aqueous sodium hydroxide (5.44 ml) was added to a stirred mixture of the methylamine salt (6.0 g) in degassed water (30 ml) at 20° C. and the mixture was stirred for one hour. The mixture was filtered and concentrated under reduced pressure at 40° C. until 24 ml of distillate collected. Water (24 ml) was added and the mixture again concentrated under reduced pressure at 40° C. until 24 ml of distillate collected. Water (30 ml) was added and a solution of calcium chloride dihydrate (1.03 g) in water (6 ml) was added dropwise at 20° C. The mixture was stirred for 45 minutes and the resultant solid filtered. The solid was washed with water (36 ml) and dried under vacuum at 40° C. to give the calcium salt of (E)-7-[4-(4-flurorophenyl)-6-isopropyl-2-(methyl(methylsulfonyl)amino]pyrimidin-5-yl](3R,5S)-3,5-dihydroxyhept-6-enoic acid.

What is claimed is:

1. A compound of the Formula VI

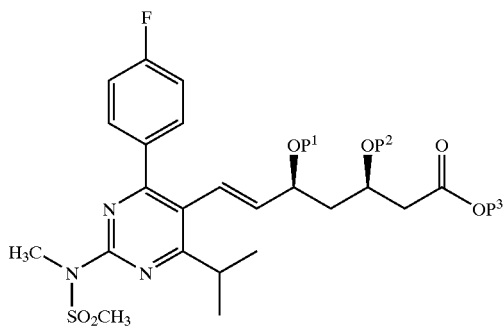

Formula VI wherein $P^1$ and $P^2$ are
alcohol protecting groups, or
$P^1$ and $P^2$, taken together, form a 1,3-diol protecting group; and $P^3$ is
a carboxylic acid protecting group.

2. The compound of claim 1,
wherein
$P^1$ and $P^2$, taken together, form

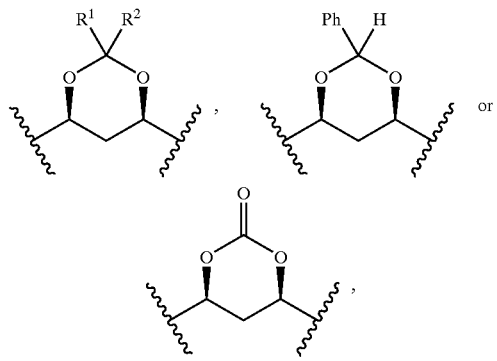

where
$R^1$ and $R^2$ are
independently (1–4C)alkyl, or
$R^1$ and $R^2$, taken together with the carbon atom to which they are attached, form a cyclopentyl, cyclohexyl or cycloheptyl ring; and $P^3$ is
(1–4C)alkyl or a metal cation.

3. A process for the manufacture of a compound of the Formula IV

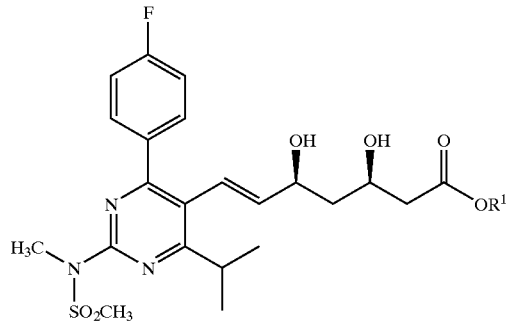

Formula IV in which $R^1$ is hydrogen or a pharmaceutically acceptable cation which comprises (1) cleavage of the $P^1$ and $P^2$ alcohol or 1,3-diol protecting groups from a compound of Formula VI;

(2) cleavage of the $P^3$ carboxylic acid protecting group from the product of step (1) to form a compound of the Formula IV in which $R^1$ is a pharmaceutically acceptable cation;

optionally followed by neutralization to give a compound of the Formula IV in which $R^1$ is hydrogen; and/or optionally followed by conversion to another compound of the Formula IV which $R^1$ is a pharmaceutically acceptable cation.

4. A process for the manufacture of a compound of the formula III

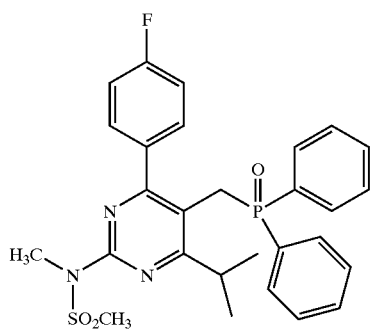

Formula III which comprises:

(1) reaction of an alkyl 4-(4-fluorophenyl)-6-isopropyl-2-[methyl(methylsulfonyl)axnino]pyrimidine5carboxylate with a reducing agent;

(2) reaction of the product of step (1) with a halogenating agent;

(3) reaction of the product of step (2) with an alkyl-diarylphosphinite.

5. A process as claimed in claim 4 wherein the reducing agent is diisobutylaluminum hydride.

6. A process as claimed in claim 4 wherein the halogenating agent is phosphorus tribromide.

7. A process as claimed in claim 4 wherein the alkyl diarylphosphinite is ethyl diphenylphosphinite.

8. A process as claimed in claim 4 where the alkyl 4-(4-fluorophenyl)-6-isopropyl-2-[methyl(methylsulfonyl)amino]pyrimidine-5-carboxylate is methyl 4(4-fluorophenyl)-6-isopropyl-2-[methyl(methylsulfonyl)amino]pyrimidine-5carboxylate.

9. A process for the manufacture of methyl 4-(4-fluorophenyl)-6-isopropyl-2-[(methyl(methylsulfonyl)amino)pyrimidine-5-carboxylate which comprises:

(1) reaction of methyl 2-amino-4-(4-fluorophenyl)-6-isopropyl-pyrimidine-5-carboxylate with methanesulfonyl chloride in the presence of strong base; and (2) reaction of the product of step (1) with a methylating agent in the presence of strong base.

10. A process as claimed in claim 9, wherein the methylating agent is dimethyl sulfate.

11. A process as claimed in claim 9, wherein the strong base is sodium tert-pentoxide.

* * * * *